United States Patent [19]

Casati et al.

[11] Patent Number: 4,613,460
[45] Date of Patent: Sep. 23, 1986

[54] PROCESS FOR PREPARING α-L-ASPARTYL-L-PHENYLALANINE METHYL ESTER

[75] Inventors: Paolo Casati, Monza; Biagio Elefante, Gorgonzola; Claudio Fuganti, Milan, all of Italy

[73] Assignee: DE.BI Derivati Biologici International S.p.A., Milan, Italy

[21] Appl. No.: 661,390

[22] Filed: Oct. 16, 1984

[30] Foreign Application Priority Data

Jan. 13, 1984 [IT] Italy ............................ 19141 A/84

[51] Int. Cl.$^4$ .............................................. C07K 5/06
[52] U.S. Cl. ................................................... 560/41
[58] Field of Search ................................. 260/112.5 R

[56] References Cited

U.S. PATENT DOCUMENTS 3,901,871 8/1975 Anderson .................... 260/112.5 R

FOREIGN PATENT DOCUMENTS 1243169 8/1971 United Kingdom .

OTHER PUBLICATIONS

King et al., *J. Org. Chem.*, 46, 4780–4782 (1981).
Vogel, *Practical Organic Chem.*, 3rd Ed., Langmans, Green and Co., N.Y., p. 474.

*Primary Examiner*—Delbert R. Phillips
*Assistant Examiner*—F. T. Moezie
*Attorney, Agent, or Firm*—Birch, Stewart, Kolasch & Birch

[57] ABSTRACT

A process for preparing α-L-aspartyl-L-phenylalanine methyl ester:

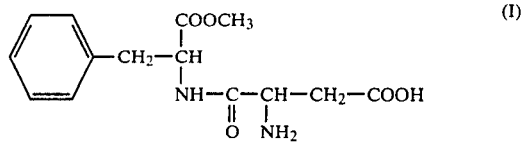

in which:
(a) the compound methyl N(α-L-aspartyl)α-aminocinnamate, protected at the nitrogen, of formula:

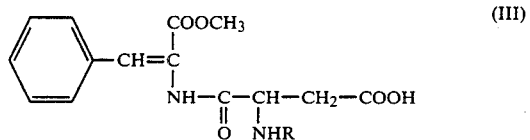

where R is a protector group at the nitrogen, is subjected to hydrogenation at the olefin bond by means of gaseous hydrogen in the presence of a hydrogenation catalyst, to give the compound of formula:

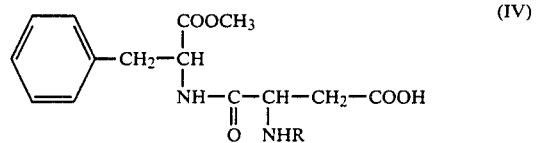

where R has the aforesaid meaning, in the form of a mixture of α-L-aspartyl-L-phenylalanine methyl ester protected at the nitrogen, and α-L-aspartyl-D-phenylalanine methyl ester protected at the nitrogen;

(b) the protector group is removed from the α-L-aspartyl-L-phenylalanine and α-L-aspartyl-D-phenylalanine methyl esters protected at the nitrogen;

(c) the α-L-aspartyl-L-phenylalanine methyl ester is separated and recovered from the deprotection reaction product.

2 Claims, No Drawings

PROCESS FOR PREPARING α-L-ASPARTYL-L-PHENYLALANINE METHYL ESTER

This invention relates to a process for preparing α-L-aspartyl-L-phenylalanine methyl ester:

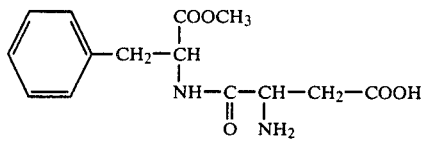

which is useful as a sweetening agent.

The compound (I), the sweetening characteristics of which are described for example in Belgian Pat. No. 717,373, is obtained, in accordance with one known process, by reacting L-phenylalanine methyl ester with a L-aspartic acid derivative in which the amino function is protected by a benzyloxycarbonyl group, and the β-carboxyl function is protected by a benzyl ester group, the α-carboxyl group having been previously transformed into the ester function by reaction with p-nitrophenol. The protector groups are then eliminated from the reaction product obtained. According to French patent 7015787, the compound (I) is obtained by a process comprising reacting L-aspartic anhydride, protected at the nitrogen, with L-phenylalanine methyl ester, operating in an organic solvent.

The nitrogen protector group is then eliminated from the reaction product thus obtained. According to Japanese published patent application 113,841/76 of 7.10.1976, the N-formyl-α-aspartyl-L-phenylalanine methyl ester is prepared by reacting L-phenylalanine methyl ester with L-formyl-aspartic anhydride operating in the presence of an organic acid. The reaction product thus obtained is then subjected to deformylation.

The known processes involve the use, as starting material, of L-phenylalanine which is prepared by chemical synthesis or by costly complicated fermentation processes, which results in high production costs. A further drawback of the known processes consists of the fact they give rise to the formation of more or less considerable quantities of the compound:

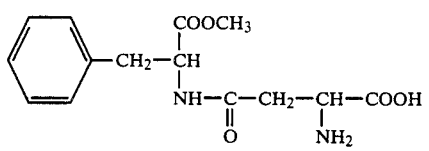

the presence of which is undesirable in that only compound (I) has sweetening power, whereas compound (II) has a slightly bitter taste. Treatment is therefore required for separating and purifying the required compound (I).

In conclusion, the known processes are costly because of the use of expensive raw materials, because of the number of treatment steps necessary, and because of the overall medicore reaction yields. Consequently, the object of the present invention is a process for preparing α-L-aspartyl-L-phenylalanine methyl ester which is free or substantially free from the aforesaid drawbacks.

This is attained according to the present invention by preparing α-L-aspartyl-L-phenylalanine methyl ester

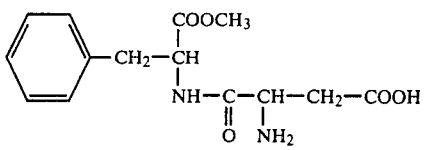

by means of a process characterised in that:

(a) the compound methyl N(α-L-aspartyl)α-aminocinnamate, protected at the nitrogen, of formula:

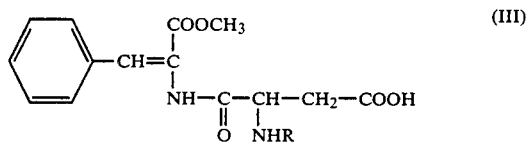

where R is a nitrogen protector group, is hydrogenated at the olefin bond with gaseous hydrogen in the presence of a hydrogenation catalyst to give the compound of formula:

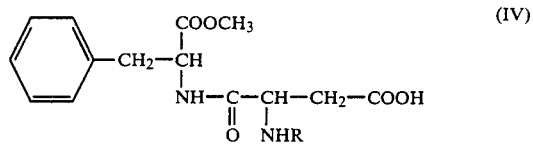

where R has the aforesaid meaning, in the form of a mixture of α-aspartyl-L-phenylalanine methyl ester protected at the nitrogen and α-L-aspartyl-D-phenylalanine methyl ester protected at the nitrogen;

(b) the protector group is removed from said α-L-aspartyl-L-phenylalanine and α-L-aspartyl-D-phenylalanine methyl esters protected at the nitrogen;

(c) the α-L-aspartyl-L-phenylalanine methyl ester is separated and recovered from the deprotection reaction product.

Stage (a)

In stage (a) of the process according to the present invention, the compound methyl N(α-L-aspartyl)α-aminocinnamate, protected at the nitrogen, and represented by the formula:

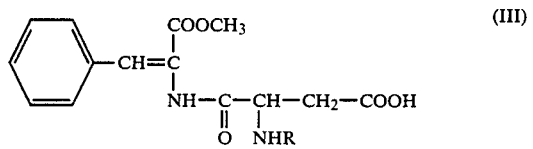

where R represents a protector group at the nitrogen, generally chosen from the formyl, carbobenzoxy and paramethoxycarbobenzoxy groups, or another nitrogen protector group known to the art, is subjected to catalytic hydrogenation.

According to the present invention, the compound (III) is hydrogenated at the olefin bond with gaseous hydrogen in the presence of a hydrogenation catalyst, to give the compound of formula:

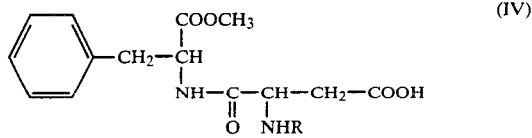

in the form of a mixture of α-L-aspartyl-L-phenylalanine methyl ester protected at the nitrogen and α-L-aspartyl-D-phenylalanine methyl ester protected at the nitrogen.

The hydrogenation catalysts used for this purpose can be any hydrogenation catalyst known in the art for its capacity to hydrogenate the olefin double bond, for example catalysts of the noble metals such as palladium on carbon and platinum on carbon. However in the preferred embodiment, complex catalysts soluble in the operating medium are used, constituted by rhodium coordination complexes with an optically active phosphinic ligand.

In particular the phosphinic ligand can be chosen from monophosphinic or diphosphinic ligands, or from monoaminophosphinic or diaminophosphinic ligands such as those described in French Pat. Nos. 2,100,644, 2,253,026 and 2,349,555, the description of which is incorporated herein as reference.

The absolutely preferred catalysts are those rhodium coordination complexes with an optically active phosphinic ligand which are able to direct the hydrogenation reaction towards the formation of the compound (IV) in which the α-L-aspartyl-L-phenylalanine methyl ester protected at the nitrogen prevails over the α-L-aspartyl-D-phenylalanine methyl ester protected at the nitrogen. Specific examples of such absolutely preferred catalysts are:

rhodium complexes with chiral chelating bis aminophosphines:

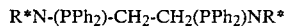

where: $R^* = S(-)α$-methylbenzyl or $(-)$menthyl, for example
$[Rh(C+)phenethylPNNP)COD]^+ClO_4^-$

[COD = 1,5-cyclooctadiene]

described by M. Fiorini, F. Marcati and G. M. Giongo in Journal of Molecular Catalysis, 4 (1978), 125–134;

rhodium complexes with ligands derived from lactic acid, ie PROPHOS

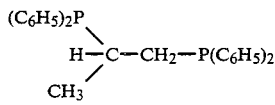

which are synthesised from (S)-lactic acid, for example [Rh(R)-PROPHOS(norbornadiene)]-ClO$_4$.0.5CH$_2$Cl$_2$ described by M. D. Fryzuk and B. Bosnich in J. Am. Chem. Soc. (1978), 5491.

The catalyst quantity used in hydrogenating the compound (III) is generally such as to obtain a weight ratio of compound (III) to catalyst of between 100:1 and 20,000:1.

Hydrogenation of the compound (III) is conducted in the liquid phase, with the catalyst suspended or dissolved, according to the particular catalyst used, in an inert organic solvent. Solvents suitable for this purpose are hydrocarbons, alcohols, ethers and esters which are liquid under the conditions in which the hydrogenation reaction is carried out. Specific examples of solvents pertaining to the aforesaid classes are tetrohydrofuran and ethanol. The choice of solvent is not particularly critical, in that in the process of the present invention the influence of the solvent is not a determining factor in the distribution between the α-L-aspartyl-L-phenylalanine methyl ester protected at the nitrogen and the α-L-aspartyl-D-phenylalanine methyl ester protected at the nitrogen in the compound (IV).

The temperature at which the hydrogenation reaction is carried out can generally vary from 10° C. to 60° C., and the corresponding reaction time generally varies from 20 hours to 20 minutes. Typically, the operation is carried out at ambient temperature (20°–25° C.), and in this case the time required for completing or substantially completing the reaction is typically of the order of 14 hours. The hydrogenation reaction can be conducted under a hydrogen pressure equal to or greater than atmospheric, and it is generally not advantageous to exceed about 50 atmospheres.

When operating under the aforesaid conditions, a compound (IV) is obtained in which the molar ratio of α-L-aspartyl-L-phenylalanine methyl ester protected at the nitrogen to α-L-aspartyl-D-phenylalanine methyl ester protected at the nitrogen varies between about 30:70 and about 95:5 or more, according to the chosen hydrogenation catalyst.

In the preferred embodiment, the catalysts used are those capable of giving the higher values of the aforesaid ratio.

At the end of the hydrogenation reaction, the catalyst is removed by extraction, filtration, absorption on basic ion exchange resins or some other suitable method, and the solvent is also removed, by evaporation, the residual mixture being treated to remove the nitrogen protector group of the compound (IV). Alternatively, the solvent is evaporated, the residue taken up in water, filtered and the filtrate cooled to precipitate the compound (IV), in which the α-L-aspartyl-L-phenylalanine methyl ester protected at the nitrogen prevails over the α-L-aspartyl-D-phenylalanine methyl ester protected at the nitrogen.

Stage (b)

In this reaction stage, any known method can be used for removing the protector group at the nitrogen of compound (IV).

For example, when the protector group is a formyl group, the operation can typically be carried out with normal hydrochloric acid in hydroalcoholic solution, particularly hydromethanolic, with a water/alcohol ratio of the order of 1:6.5, under boiling conditions. Under these conditions, complete or substantially complete deformylation is attained in a time of the order of 0.5 hours. The reaction mixture thus obtained is neutralised, for example by treating with sodium carbonate, and the alcohol is then separated by evaporation. When the protector group at the nitrogen is carbobenzoxy or another similar removable group, deprotection can be carried out by hydrogenolysis, for example with a palladium-on-carbon catalyst in a glacial acetic acid environment. In this case, the hydrogenolysis can be conducted at a temperature of between 5° and 90° C. with a reaction time of between 0.5 and 12 hours.

Typically, the operation is carried out at ambient temperature (20°–25° C.) with a reaction time of the order of 3 hours.

If deprotecting the compound (IV) by hydrogenolysis, the reaction can be conducted on the reaction product from stage (a) without previously separating the catalyst used for hydrogenating the compound (III).

In all cases at the end of the reaction, the catalyst or catalysts used are removed from the reaction mixture, and the solvent is then removed by evaporation.

Stage (c)

Separation of the α-L-aspartyl-L-phenylalanine methyl ester from the α-L-aspartyl-D-phenylalanine methyl ester of the reaction mixture of stage (b) is conveniently conducted by crystallisation from water, from alcohol or from hydroalcoholic mixtures. In this crystallisation, the required product in the form of α-L-aspartyl-L-phenylalanine methyl ester precipitates, and the α-L-aspartyl-D-phenylalanine methyl ester remains in solution.

The compound (III) which is subjected to hydrogenation constitutes one of the subject matters of the present invention and can be prepared by the following procedure:

L-aspartic anhydride protected at the nitrogen:

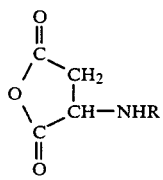
(V)

where R is a protector group chosen from those stated heretofore, is brought into contact with β-chloro-D,L-phenylalanine methyl ester:

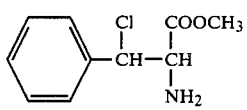
(VI)

to give a mixture of α-L-aspartyl-β-chloro-D,L-phenylalanine methyl ester protected at the nitrogen:

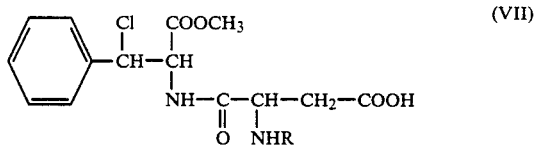
(VII)

and β-L-aspartyl-β-chloro-D,L-phenylalanine methyl ester protected at the nitrogen:

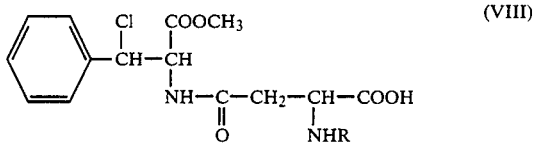
(VIII)

where R has the aforesaid meaning;

the β-L-aspartyl-β-chloro-D,L-phenylalanine methyl ester protected at the nitrogen is separated from the α-L-aspartyl-β-chloro-D,L-phenylalanine methyl ester protected at the nitrogen;

the α-L-aspartyl-β-chloro-D,L-phenylalanine methyl ester protected at the nitrogen is subjected to a dehydrohalogenation reaction to give the compound (III), which is separated from the reaction mixture.

More particularly, in preparing the compound (III), compounds (V) and (VI) are firstly interacted in a molar ratio of between 1:1 and 1:5, operating in the homogeneous liquid phase in an inert organic solvent in the presence of an acid agent, for example acetic acid or acid ion exchange resins.

Organic solvents suitable for this purpose are hydrocarbons, chlorinated hydrocarbons, alcohols, ketones, ethers and esters. Specific examples of solvents pertaining to the aforesaid classes are ethyl acetate, methyl propionate, dioxane, ethyl ether and chloroform. The reaction temperature can vary within the range of −30° C. to 60° C., with a reaction time of between 4 and 0.5 hours. Typically, the operation is carried out at a temperature of the order of 0° C. for a time of about 2 hours, with a molar ratio of compound (V) to compound (VI) of 1:1, in the presence of catalytic quantities of an acid exchange resin to give the compounds (VII) and (VIII) with a yield of about 90%, and in a molar ratio of the order of 80:20.

The catalyst is then separated or neutralised, and the solvent separated, after which compound (VII) is separated from compound (VIII) by crystallisation.

The compound (VII) is then subjected to dehydrochlorination to give the compound (III). For such a reaction, basic organic or inorganic agents can be used, preferably alkaline alcoholates, such as sodium methylate and ethylate. The operation is conveniently carried out with a molar ratio of compound (VII) to the basic agent of between 1:1 and 1:10, in an inert organic solvent generally chosen from hydrocarbons, chlorinated hydrocarbons, alcohols, ethers and esters. Specific examples of solvents pertaining to the aforesaid classes are ethanol, tetrahydrofuran, dioxane, ethyl acetate, chloroform and methylene chloride.

The dehydrohalogenation reaction temperature can generally vary from 0° to 60° C. and the corresponding reaction time from 12 to 0.5 hours. typically, the operation is carried out at ambient temperature (20°–25° C.) with a ratio of compound (VII) to sodium methylate or ethylate of 1:2 and a reaction time of about 4 hours.

The mixture obtained from the dehydrohalogenation reaction is treated with a mineral acid such as hydrochloric acid, sulphuric acid, nitric acid or phosphoric acid, at a temperature of between 0° and 60° C. and preferably at ambient temperature (20°–25° C.).

The organic phase is then washed, preferably with a saturated aqueous solution of sodium chloride, and the solvent is then removed by evaporation.

The compound (III) is separated by crystallising the residue of the evaporation from an organic solvent, such as ethyl acetate. Alternatively, the compound (III) can be obtained from compounds similar to the compound (VII) which contain a halogen other than chlorine, or which instead of chlorine contain groups such as the hydroxyl or the relative tosylate and mesylate derivatives, which are removable with the formation of the olefin bond.

The compound (VI), namely β-chloro-D,L-phenylalanine methyl ester, can be obtained by procedures known to the art and preferably by the following procedure:

glycine:

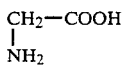

is interacted with benzaldehyde:

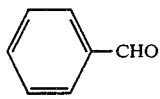

operating in the presence of alkaline hydroxide, to give D,L-phenylserine:

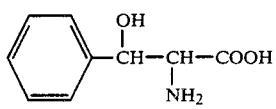

and the compound (XI) is separated and recovered; the compound (XI) recovered in this manner is brought into contact with methanol in the presence of hydrochloric acid, to give D,L-phenylserine methyl ester in the form of the hydrochloride:

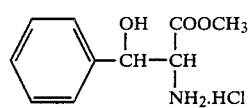

for example as described by G. Carrara and G. Weitnaner in Gazetta 1949, 856, after which the compound (XII) is separated and brought into contact with SOCl₂ in chloroform, to give the corresponding chlorinated derivative:

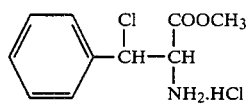

the reaction mixture thus obtained is neutralised, for example with potassium carbonate, and the β-chloro-D,L-phenylalanine methyl ester (compound VI) is finally recovered.

The experimental examples given hereinafter illustrate the invention, but are not limitative thereof.

EXAMPLE 1

Preparation of β-chloro-D,L-phenylalanine methyl ester (VI)

300 g (4 moles) of glycine (IX), 210 g (6 moles) of sodium hydroxide and 1 liter of distilled water are placed in a glass flask of capacity 3 liters fitted with an agitator.

800 g (7.5 moles) of benzaldehyde (X) are added to this continuously agitated solution over a period of about 3 hours, the temperature being controlled at less than 10° C.

At the end of said time a dispersion is obtained which is kept at a temperature of 0° C. for 24 hours. 500 ml of 12N hydrochloric acid are added to this dispersion, and the mass is kept agitated at the temperature of 0° C. overnight.

The solid is then filtered off and is purified by crystallisation, by treating with boiling water and then adding an equal volume of ethyl alcohol.

In this manner 250 g (yield 73%) of D,L-phenylserine (XI) are obtained, with a melting point of 194°–195° C.

Hydrochloric acid gas is bubbled into a solution of 200 g (1.1 moles) of D,L-phenylserine (XI) in 400 ml of methanol for a period of 0.5 hours. The resultant solution is kept boiling in a reflux apparatus for 3 hours.

The solvent is then evaporated to dryness, and the residue is crystallised from 0.5:1:1 methanol/ethyl acetate/ether.

In this manner 150 g of D,L-phenylserine methyl ester in the form of the hydrochloride (XII) are obtained. The mother liquors of crystallisation are subjected to the aforesaid treatments to obtain a further 78 g of D,L-phenylserine methyl ester in the form of the hydrochloride (XII) (overall yield 90%; melting point 156° C.). 100 ml (1.43 moles) of SOCl₂ are added to a solution of 230 g (1 mole) of D,L-phenylserine methyl ester in the form of the hydrochloride (XII) in 300 ml of chloroform. The solution thus obtained is kept at ambient temperature (20°–25° C.) for 12 hours. The solvent is then evaporated to dryness and the compound (XIII) is obtained by crystallisation from 1:1 methanol/ether, in a quantity of 210 g (yield 85%) with a melting point of 175° C.

The compound (XIII) obtained in this manner is treated with a solution of 53 g of sodium carbonate in 0.5 l of water for a period of 0.5 hours at ambient temperature (20°–25° C.). The mixture is then extracted twice, each time with 500 ml of ethyl acetate. The ethyl acetate phases are pooled and are evaporated to dryness to obtain 190 g of β-chloro-D,L-phenylalanine methyl ester (VI).

EXAMPLE 2

Preparation of methyl N(α-L-aspartyl)α-aminocinnamate (III)

14.3 g (0.1 moles) of N-formyl-L-aspartic anhydride (V) dissolved in 50 ml of ethyl acetate and 6 ml of glacial acetic acid are placed in a glass flask of capacity 0.5 l fitted with an agitator. 21 g (0.1 moles) of β-chloro-D,L-phenylalanine methyl ester (VI) dissolved in 150 ml of ethyl acetate are added drop by drop to this solution, which is kept at 0° C. under agitation.

The agitated solution is kept at 0° C. for a period of 2 hours. At the end of this period, it is cooled to −10° C. and the N-formyl-α-L-aspartyl-β-chloro-D,L-phenylalanine methyl ester (VII) precipitates in a quantity of 27 g (yield 75%).

27 g (50 mmoles) of sodium methylate are added to a solution of 25 g (25 mmoles) of the compound (VII) obtained as heretofore described in 50 ml of tetrahydrofuran, and the mixture kept at ambient temperature (20°–25° C.) for a period of 2 hours.

At the end of said period, 200 ml of ethyl acetate and 50 ml (about 110 mmoles) of 10% hydrochloric acid are added to the reaction mixture. The resultant mixture is kept at ambient temperature (20°–25° C.) for a period of 10 minutes.

The organic phase is then washed with a saturated aqueous solution of sodium chloride and is then dried over anhydrous sodium sulphate. Finally, the solvent is removed by evaporation and 6 g (yield 75%) of the compound (III) are recovered by crystallisation from ethyl acetate.

EXAMPLE 3

A hydrogenation reactor of capacity 0.5 l fitted with an agitator is fed with 6.4 g (20 mmoles) of the compound (III) prepared in accordance with the preceding Example 2 in solution in 150 ml of tetrahydrofuran deoxygenated by means of gaseous nitrogen, and 100 mg of the hydrogenation catalyst [Rh-(R)-PROPHOS(-norbornadiene)]ClO$_4$.0.5CH$_2$Cl$_2$ dissolved in 50 ml of tetrahydrofuran, pretreated under 2 atmospheres of gaseous hydrogen at ambient temperature. Said catalyst was obtained as described by M. D. Fryzuk and B. Bosnich in J. Am. Chem. Soc. (1977), 6962.

The resultant solution is kept agitated at ambient temperature (20°-25° C.) under 2 atmospheres of hydrogen pressure for 14 hours. After this period, the solvent is evaporated to dryness and the residue taken up in water, and then filtered. The filtrate contains N-formyl-α-L-aspartyl-L-phenylalanine methyl ester and N-formyl-α-L-aspartyl-D-phenylalanine methyl ester with a yield of 100% with respect to the fed compound (III), and in a molar ratio of 90:10 as determined by NMR analysis.

The filtrate is cooled to 0° C., and 4.2 g (yield 66%) of a mixture of N-formyl-α-L-aspartyl-L-phenylalanine methyl ester and N-formyl-α-L-aspartyl-D-phenylalanine methyl ester (IV) precipitate. This precipitate is subjected to NMR analysis, and the ratio of N-formyl-α-L-aspartyl-L-phenylalanine methyl ester to N-formyl-α-L-aspartyl-D-phenylalanine methyl ester is found to be 98:2. The compound (IV) is subjected to deformylation using normal hydrochloric acid in a hydromethanolic solution (water/methanol ratio 1:6.5) under boiling conditions. Deformylation is complete in a time of 0.5 hours. The reaction mixture is then neutralised with sodium carbonate, and the methanol separated by evaporation. The residue is crystallised from water to obtain 2.3 g (yield 60%) of crystals of pure α-L-aspartyl-L-phenylalanine methyl ester (I), the identity of which is confirmed by HPLC analysis.

EXAMPLE 4

The procedure of Example 3 is followed using the catalyst [RhCl(cyclooctene)$_2$]$_2$ (50 mg)+[S,S-DIOP] (150 mg), this latter being acquired from Chemalog (USA). The catalyst is prepared as described by H. B. Kagan and T. P. Dang in Chem. Commun. 481 (1971). After hydrogenation, 6.4 g (yield 100%) of a mixture of N-formyl-α-L-aspartyl-L-phenylalanine methyl ester and N-formyl-α-L-aspartyl-D-phenylalanine methyl ester are obtained, in a molar ratio of 30:70. This mixture is treated as in Example 3 and subjected to deformylation, the α-L-aspartyl-L-phenylalanine methyl ester being separated from the deformylation reaction product as described in said Example 3.

EXAMPLE 5

The procedure of Example 3 is followed, using 200 mg of 10% palladium-on-carbon hydrogenation catalyst.

6.4 g (yield 100%) of a mixture of N-formyl-α-L-aspartyl-L-phenylalanine methyl ester and N-formyl-α-L-aspartyl-D-phenylalanine methyl ester are obtained, in a molar ratio of 55:45. This mixture is treated as in Example 3 and subjected to deformylation, the α-L-aspartyl-L-phenylalanine methyl ester being separated from the deformylation reaction product as described in said Example 3.

EXAMPLE 6

The procedure of Example 3 is followed, hydrogenating 8.5 g (20 mmoles) of the compound (III) containing the carbobenzyloxy group as protector group at the nitrogen.

100 mg of 10% palladium-on-carbon catalyst and 100 ml of glacial acetic acid are added, and 2 atmospheres of hydrogen pressure are applied for 3 hours.

At the end of this period, the mixture is evaporated to dryness, the residue is taken up in water and filtered in order to separate the catalyst.

The filtrate is cooled to 0° C., and 5.3 g of crystals consisting of L-α-aspartyl-L-phenylalanine methyl ester containing a small quantity (about 2%) of α-L-aspartyl-D-phenylalanine methyl ester precipitate. The mixture is crystallised from water to separate the α-L-aspartyl-L-phenylalanine methyl ester.

EXAMPLE 7

The procedure of Example 3 is followed, using 100 mg of the catalyst [Rh(C+)phenethyl PNNP)COD]+ClO$_4^-$ in 100 ml of methanol. The catalyst is prepared as described by M. Fiorini, F. Marcati and G. M. Giongo in J. Mol. Cat. 4, 1978, 125–134.

On NMR analysis, the crude hydrogenation product is found to contain N-formyl-α-L-aspartyl-L-phenylalanine methyl ester and N-formyl-α-L-aspartyl-D-phenylalanine methyl ester in a molar ratio of 75:25. After crystallising from water, 4.2 g (yield 66%) of a mixture of N-formyl-α-L-aspartyl-L-phenylalanine methyl ester and N-formyl-α-L-aspartyl-D-phenylalanine methyl ester are obtained in a molar ratio of 95:5.

This mixture is deformylated, and α-L-aspartyl-L-phenylalanine methyl ester is separated from the deformylation reaction product, by operating as described in Example 3.

We claim:

1. The compound methyl N(α-L-aspartyl)α-aminocinnamate protected at the nitrogen, of formula

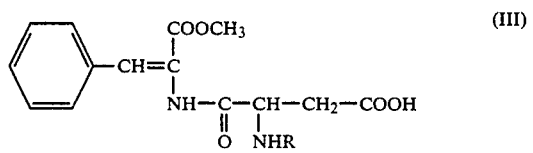

(III)

where R is a protector group at the nitrogen.

2. The compound as claimed in claim 1, wherein R is a formyl, carbobenzoxy or paramethoxy-carbobenzoxy group.

* * * * *